US012226422B2

(12) United States Patent
Löscher et al.

(10) Patent No.: US 12,226,422 B2
(45) Date of Patent: Feb. 18, 2025

(54) OPHTHALMIC COMPOSITIONS COMPRISING TAFLUPROST FOR THE TREATMENT OF GLAUCOMA

(71) Applicant: NOVALIQ GMBH, Heidelberg (DE)

(72) Inventors: Frank Löscher, Schriesheim (DE); Diana Strehl, Heidelberg (DE); Kirsten Eickhoff, Aschaffenburg (DE)

(73) Assignee: NOVALIQ GMBH, Heidelberg (DE)

( * ) Notice: Subject to any disclaimer, the term of this patent is extended or adjusted under 35 U.S.C. 154(b) by 955 days.

(21) Appl. No.: 17/051,016

(22) PCT Filed: Apr. 24, 2019

(86) PCT No.: PCT/EP2019/060455
§ 371 (c)(1),
(2) Date: Oct. 27, 2020

(87) PCT Pub. No.: WO2019/206956
PCT Pub. Date: Oct. 31, 2019

(65) Prior Publication Data
US 2021/0228595 A1    Jul. 29, 2021

(30) Foreign Application Priority Data

Apr. 27, 2018   (EP) .................... 18169920

(51) Int. Cl.
*A61K 31/5575* (2006.01)
*A61F 9/00* (2006.01)
*A61K 9/00* (2006.01)
*A61K 31/02* (2006.01)
*A61P 27/06* (2006.01)

(52) U.S. Cl.
CPC ........ *A61K 31/5575* (2013.01); *A61F 9/0008* (2013.01); *A61K 9/0048* (2013.01); *A61K 31/02* (2013.01); *A61P 27/06* (2018.01)

(58) Field of Classification Search
CPC ............................ A61F 9/0008; A61K 9/0048
See application file for complete search history.

(56) References Cited

U.S. PATENT DOCUMENTS

| | | |
|---|---|---|
| 2,616,927 A | 11/1952 | Kauck et al. |
| 4,452,818 A | 6/1984 | Haidt |
| 4,649,047 A | 3/1987 | Kaswan |
| 5,077,036 A | 12/1991 | Long |
| 5,126,127 A | 6/1992 | Bhagwat et al. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,340,567 A | 8/1994 | Cole et al. |
| 5,370,313 A | 12/1994 | Beard |
| 5,518,731 A | 5/1996 | Meadows |
| 5,667,809 A | 9/1997 | Trevino et al. |
| 5,849,291 A | 12/1998 | Kessler |
| 5,851,544 A | 12/1998 | Penska et al. |
| 5,874,469 A | 2/1999 | Maniar et al. |
| 5,874,481 A | 2/1999 | Weers et al. |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Reiss et al. |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,105 B1 | 7/2001 | Johnstone |
| 6,262,126 B1 | 7/2001 | Meinert |
| 6,264,990 B1 | 7/2001 | Knepp et al. |
| 6,294,563 B1 | 9/2001 | Garst |
| 6,335,335 B2 | 1/2002 | Higashiyama |
| 6,372,243 B2 | 4/2002 | Kobuch |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,576,663 B2 | 6/2003 | Klimko |
| 6,730,328 B2 | 5/2004 | Maskiewicz et al. |
| 7,001,607 B1 | 2/2006 | Menz et al. |
| 7,026,359 B1 | 4/2006 | Gross |

(Continued)

FOREIGN PATENT DOCUMENTS

| | | |
|---|---|---|
| CN | 202136470 | 2/2012 |
| CN | 203524843 U | 4/2014 |

(Continued)

OTHER PUBLICATIONS

Zioptan Drug Label DailyMed, NIH, 2017 (Year: 2017).*
Reduction in drop size of ophthalmic topical drop preparations and the impact of treatment Kumar et al. J. Adv. Pharm. Tech. Res. 2011 (Year: 2011).*
Clinical appraisal of tafluprost in the reduction of elevated intraocular pressure (IOP) in open-angle glaucoma and ocular hypertension Aihara et al. Clinical Ophthalmology 2010:4 163-170 (Year: 2010).*
Anonymous, "Semifluorinated alkane technology brings advantages for topical therapy," Ophthalmology Times, pp. 1-2 (2016) http://www.ophthalmologytimes.com/ophthalmology/semifluorinated-alkane-technology-brings-advantages-topical-therapy.
Anonymous, "Highlights of Prescribing Information: Zioptan", pp. 1-11 (2014) https://www.accessdata.fda.gov/drugsatfda_docs/label/2015/202514s003s004lbl.pdf.

(Continued)

*Primary Examiner* — Jeffrey S Lundgren
*Assistant Examiner* — Eric Tran
(74) *Attorney, Agent, or Firm* — Hoxie & Associates LLC

(57) ABSTRACT

The invention provides a pharmaceutical composition for use in the prevention or therapy of glaucoma, increased intraocular pressure, ocular hypertension and/or a symptom associated therewith, wherein the composition comprises tafluprost and a semifluorinated alkane.

19 Claims, 1 Drawing Sheet

(56) References Cited

U.S. PATENT DOCUMENTS

| | | |
|---|---|---|
| 7,041,705 B2 | 5/2006 | Mishra et al. |
| 7,258,869 B1 | 8/2007 | Berry et al. |
| 7,283,239 B2 | 10/2007 | Nonogaki et al. |
| 7,608,261 B2 | 10/2009 | Furfine et al. |
| 7,687,445 B2 | 3/2010 | Bonnet et al. |
| 7,687,455 B2 | 3/2010 | Bonnet et al. |
| 7,740,875 B2 | 6/2010 | Dechow |
| 7,776,349 B2 | 8/2010 | Dechow et al. |
| 8,029,977 B2 | 10/2011 | Meinert |
| 8,222,292 B2 | 7/2012 | Goskonda et al. |
| 8,470,873 B2 | 6/2013 | Chen et al. |
| 8,492,334 B2 | 7/2013 | Lavik et al. |
| 8,614,178 B2 | 12/2013 | Theisinger et al. |
| 8,759,281 B2 | 6/2014 | Bonnet et al. |
| 8,759,404 B2 | 6/2014 | Daftary et al. |
| 8,772,337 B2 | 7/2014 | Pilotaz et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,005,626 B2 | 4/2015 | Seigfried |
| 9,023,898 B2 | 5/2015 | Wong et al. |
| 9,186,305 B1 | 11/2015 | Suzuki |
| 9,241,900 B2 | 1/2016 | Wilson |
| 9,308,262 B2 | 4/2016 | Günther et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 9,968,678 B2 | 5/2018 | Theisinger et al. |
| 9,982,032 B2 | 5/2018 | Park et al. |
| 10,045,996 B2 | 8/2018 | Theisinger et al. |
| 10,045,997 B2 | 8/2018 | Chen et al. |
| 10,058,615 B2 | 8/2018 | Günther et al. |
| 10,064,944 B2 | 9/2018 | Wilson |
| 10,123,904 B2 | 11/2018 | Chauhan et al. |
| 10,130,707 B2 | 11/2018 | Günther et al. |
| 10,273,298 B2 | 4/2019 | Günther et al. |
| 10,286,035 B2 | 5/2019 | Gavaris |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Loscher et al. |
| 10,813,999 B2 | 10/2020 | Günther et al. |
| 11,154,513 B2 | 10/2021 | Scherer et al. |
| 11,160,865 B2 | 11/2021 | Theisinger et al. |
| 11,241,497 B2 | 2/2022 | Reza et al. |
| 11,273,174 B2 | 3/2022 | Löscher et al. |
| 11,285,163 B2 | 3/2022 | Shah et al. |
| 11,357,738 B2 | 6/2022 | Scherer et al. |
| 11,413,323 B2 | 8/2022 | Leo et al. |
| 11,457,626 B2 | 10/2022 | Wayne |
| 11,583,513 B2 | 2/2023 | Günther et al. |
| 2002/0004063 A1 | 1/2002 | Zhang |
| 2002/0006442 A1 | 1/2002 | Mishra et al. |
| 2002/0128527 A1 | 9/2002 | Meinert |
| 2002/0137793 A1 | 9/2002 | Klimko |
| 2002/0198266 A1 | 12/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson et al. |
| 2005/0075407 A1 | 4/2005 | Tamarkin et al. |
| 2005/0079210 A1 | 4/2005 | Gupta |
| 2005/0084553 A1 | 4/2005 | Moon et al. |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0009522 A1 | 1/2006 | Dana et al. |
| 2006/0013820 A1 | 1/2006 | Bonnet et al. |
| 2006/0078577 A1 | 4/2006 | Dechow |
| 2006/0078580 A1 | 4/2006 | Dechow |
| 2006/0153905 A1 | 7/2006 | Carrara et al. |
| 2007/0238732 A1 | 10/2007 | Graham et al. |
| 2007/0249730 A1 | 10/2007 | Daftary et al. |
| 2008/0019926 A1 | 1/2008 | Krafft et al. |
| 2008/0050335 A1 | 2/2008 | Faour et al. |
| 2008/0089923 A1 | 4/2008 | Burkstrand et al. |
| 2008/0112895 A1 | 5/2008 | Kottayil et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0254106 A1 | 10/2008 | Bell |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2009/0226875 A1 | 9/2009 | Meinert |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0137252 A1 | 6/2010 | Matsumura et al. |
| 2010/0189765 A1 | 7/2010 | Erickson et al. |
| 2010/0210720 A1 | 8/2010 | Pilotaz et al. |
| 2010/0226997 A1 | 9/2010 | Bowman et al. |
| 2010/0274215 A1 | 10/2010 | Wong et al. |
| 2010/0305081 A1 | 12/2010 | Dechow |
| 2010/0310476 A1 | 12/2010 | Tamarkin et al. |
| 2011/0223208 A1 | 9/2011 | Hill et al. |
| 2011/0269704 A1 | 11/2011 | Seigfried |
| 2012/0010280 A1 | 1/2012 | Aleo et al. |
| 2012/0053242 A1 | 3/2012 | Cela Lopez |
| 2012/0095097 A1 | 4/2012 | Tabuchi et al. |
| 2012/0100183 A1 | 4/2012 | Schlessinger et al. |
| 2012/0219640 A1 | 8/2012 | Wright |
| 2012/0238639 A1 | 9/2012 | Theisinger et al. |
| 2012/0244177 A1 | 9/2012 | Theisinger et al. |
| 2013/0011484 A1 | 1/2013 | Bevier |
| 2013/0046014 A1 | 2/2013 | Theisinger |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0309226 A1 | 11/2013 | Armstrong et al. |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0155488 A1 | 6/2014 | Warner et al. |
| 2014/0186350 A1 | 7/2014 | Ghosh et al. |
| 2014/0303219 A1 | 10/2014 | Bingaman et al. |
| 2014/0369993 A1 | 12/2014 | Günther et al. |
| 2015/0045282 A1 | 2/2015 | Elsohly et al. |
| 2015/0099019 A1 | 4/2015 | Johnson |
| 2015/0174096 A1 | 6/2015 | Bottger et al. |
| 2015/0224064 A1 | 8/2015 | Günther et al. |
| 2015/0238605 A1 | 8/2015 | Günther et al. |
| 2015/0258040 A1 | 9/2015 | Lynch et al. |
| 2016/0000941 A1 | 1/2016 | Keller et al. |
| 2016/0101178 A1 | 4/2016 | Wilson |
| 2016/0159902 A1 | 6/2016 | Günther et al. |
| 2016/0184259 A1 | 6/2016 | Anastassov et al. |
| 2016/0243189 A1 | 8/2016 | Gu et al. |
| 2016/0303031 A1 | 10/2016 | El Achkar et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0143832 A1 | 5/2017 | Günther et al. |
| 2017/0182060 A1 | 6/2017 | Wiedersberg et al. |
| 2017/0216204 A1 | 8/2017 | Theisinger et al. |
| 2017/0224531 A1 | 8/2017 | Chauhan et al. |
| 2017/0348285 A1 | 12/2017 | Hellstron |
| 2018/0360908 A1 | 12/2018 | Beier et al. |
| 2019/0000919 A1 | 1/2019 | Brockmeyer et al. |
| 2019/0125658 A1 | 5/2019 | Ficko |
| 2019/0256591 A1 | 8/2019 | Günther et al. |
| 2019/0274970 A1 | 9/2019 | Günther et al. |
| 2019/0298801 A1 | 10/2019 | Kerwin et al. |
| 2019/0321218 A1 | 10/2019 | Graf et al. |

(56) References Cited

U.S. PATENT DOCUMENTS

| | | |
|---|---|---|
| 2019/0328717 A1 | 10/2019 | Günther et al. |
| 2019/0343793 A1 | 11/2019 | Günther et al. |
| 2020/0023035 A1 | 1/2020 | Loscher |
| 2020/0060987 A1 | 2/2020 | Günther et al. |
| 2020/0129543 A1 | 4/2020 | Loscher et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0268648 A1 | 8/2020 | Günther et al. |
| 2020/0268682 A1 | 8/2020 | Günther et al. |
| 2020/0338015 A1 | 10/2020 | Scherer et al. |
| 2021/0023166 A1 | 1/2021 | Löscher et al. |
| 2021/0069014 A1 | 3/2021 | Löscher et al. |
| 2021/0106558 A1 | 4/2021 | Löscher et al. |
| 2021/0121471 A1 | 4/2021 | Löscher et al. |
| 2021/0236591 A1 | 8/2021 | Leo et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |
| 2022/0143137 A1 | 5/2022 | Witt et al. |
| 2022/0226427 A1 | 7/2022 | Leo et al. |
| 2022/0354786 A1 | 11/2022 | Friess et al. |
| 2022/0370377 A1 | 11/2022 | Scherer et al. |
| 2023/0043641 A1 | 2/2023 | Beier et al. |
| 2023/0330056 A1 | 10/2023 | Günther et al. |

FOREIGN PATENT DOCUMENTS

| | | | |
|---|---|---|---|
| EP | 0 089 815 | | 9/1983 |
| EP | 0 593 552 | | 4/1994 |
| EP | 0 670 159 A1 | | 9/1995 |
| EP | 1 152 749 B1 | | 4/2006 |
| JP | S6452722 | | 2/1989 |
| JP | 2000511157 | | 8/2000 |
| JP | 2001/158734 | | 6/2001 |
| JP | 2011/006348 | | 1/2011 |
| JP | 2011/024841 A | | 2/2011 |
| WO | WO 1998/005301 | | 12/1998 |
| WO | WO 00/054588 | | 9/2000 |
| WO | WO 2003/099258 | | 12/2003 |
| WO | WO 2008/136034 | | 11/2008 |
| WO | WO 2010/146536 | | 12/2010 |
| WO | WO-2011113855 A2 * | 9/2011 | ......... A61K 31/5575 |
| WO | WO 2016/082644 | | 6/2016 |
| WO | WO 2016/108130 | | 7/2016 |

OTHER PUBLICATIONS

Ahmed, I. et al., "Disposition of Timolol and Inulin in the Rabbit Eye Following Corneal Versus Non-Corneal Absorption," International Journal of Pharmaceutics, 1987, 38, 9-21.

Agarwal, et al., "Semifluorinated alkane based systems for enhanced corneal penetration of poorly soluble drugs," International Journal of Pharmaceutics, 538(1-2):119-129 (2018).

Baerdemaeker, "Pharmacokinetics in Obese Patients," Continuing Education in Anaesthesia, Critical Care & Pain, 2004, 4, 152-155.

Barata-Vallejo et al., "(Me3Si)3SiH-Mediated Intermolecular Radical Perfluoroalkylation Reactions of Olefins in Water," J. Org. Chem., 2010, 75:6141-6148.

Bardin et al., "Long-Range Nanometer-Scale Organization of Semifluorinated Alkane Monolayers at the Air/Water Interface," Langmuir, 2011, 27:13497-13505.

Bertilla et al., "Semifluorinated Alkanes as Stabilizing Agents of Fluorocarbon Emulsions," Springer, 2005, vol. 12, 24 pages.

Blackie et al., "MGD: Getting to the Root Cause of Dry Eye", Review of Optometry, 2012, pp. 1-12.

Broniatowski, M. et al., "Langmuir Monolayers Characteristics of Perfluorodecyl)-Alkanes," Journal of Physical Chemistry B, 2004, 108, 13403-13411.

Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.

Chhadva et al., "Meibomian Gland Disease the Role of Gland Dysfunction in Dry Eye Disease," Ophthalmology (2017) 124(11 Supplement): S20-S26.

Chemical Book, 5-Fluorouracil, available at <http://www.chemicalbook.com/ChemicalProductProperty_EN_CB8162744.htm>, accessed Mar. 7, 2014, 1 page.

Costa Gomes et al., "Solubility of dioxygen in seven fluorinated liquids," Journal of Fluorine Chemistry, 2004, 125, 1325-1329.

Davies, N., "Biopharmaceutical Considerations in Topical Ocular Drug Delivery," Clinical and Experimental Pharmacology and Physiology, 2000, 27, 558-562.

Dembinski, R. et al., "Semi-fluorinated Alkanes as Carriers for Drug Targeting in Acute Respiratory Failure," Experimental Lung Research, 2010, 36, 499-507.

Dias et al., "Solubility of oxygen in liquid perfluorocarbons," Fluid Phase Equilibria, 2004, 222-223:325-330.

Dutescu, R.M. et al., "Semifluorinated alkanes as a liquid drug carrier system for topical ocular drug delivery," European Journal of Pharmaceutics and Biopharmaceutics, 2014, pp. 123-128.

Elkeeb, R. et al., "Transungual Drug Delivery: Current Status," International Journal of Pharmaceutics, 2010, 384, 1-8.

English-language machine translation of EP0670159 (A1) issued in U.S. Appl. No. 14/122,025 on Apr. 1, 2015, 10 pages.

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.

Gayton, J., "Etiology, Prevalence, and Treatment of Dry Eye Disease," Clinical Ophthalmology, 2009, 3, 405-412.

Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).

Gerdenitsch, "Emulsions—established and promising drug carriers for parenteral adminstration", International Pharmaceutical Industry, 62-62, retrieved from internet: http://ipimediaworld.com/wp-content/uploads/2012/05/Pages-from-IPI-Volume-2-Issue-1-11.pdf Date Accessed: Jun. 20, 2016.

German, E.J., et al., "Reality of drop size from multi-dose eye drop bottles: is it cause for concern?" Eye, 1999, 13:93-100.

Griffin, W., "Classification of Surface-Active Agents by 'HLB'," Journal of the Society of Cosmetic Chemists, 1949, 1, 311-326.

Gopal et al., "Use of intravitreal injection of triamcinolone acetonide in the treatment of age-related macular degeneration," Indian J Ophthalmol., 2007, 55(6):431-435, (8 pages).

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

Holm, R. et al., "A novel excipient, 1-perfluorohexyloctane shows limited utility for the oral delivery of poorly water-soluble drugs," European Journal of Pharmaceutical Sciences, 2011, 42, 416-422.

International Preliminary Report on Patentability for International Application No. PCT/EP2011/053949 dated Sep. 18, 2012, 9 Pages.

International Preliminary Report on Patentability for International Application No. PCT/EP2011/068141 Apr. 23, 2013, 4 Pages.

International Preliminary Report on Patentability for International Application No. PCT/EP2011/069795 dated May 14, 2013, 8 pages.

(56) References Cited

OTHER PUBLICATIONS

International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Preliminary Report on Patentability for International Application No. PCT/EP2013/068882 Mar. 17, 2015, 5 pages.
International Preliminary Report on Patentability for International Application No. PCT/EP2013/068909 Mar. 17, 2015, 11 pages.
International Preliminary Report on Patentability for International Application No. PCT/EP2014/065840 Jan. 26, 2016, 7 pages.
International Preliminary Report on Patentability for International Application No. PCT/EP2017/065163 Dec. 25, 2018, 6 pages.
International Preliminary Report on Patentability for International Application No. PCT/EP2017/073697 Mar. 26, 2019, 7 pages.
International Preliminary Report on Patentability for International Application No. PCT/EP2017/074079 Mar. 26, 2019, 7 pages.
International Preliminary Report on Patentability for International Application No. PCT/EP2017/074545 Apr. 2, 2019, 7 pages.
International Preliminary Report on Patentability for International Application No. PCT/EP2017/082739 Jun. 25, 2019, 7 pages.
International Search Report for International Application No. PCT/EP2011/053949 mailed Sep. 6, 2011, 5 pages.
International Search Report for International Application No. PCT/EP2011/068141 mailed Dec. 14, 2011, 2 pages.
International Search Report for International Application No. PCT/EP2011/069795 mailed Jan. 16, 2012, 3 pages.
International Search Report for International Application No. PCT/EP2012/050043 mailed Apr. 24, 2012, 2 pages.
International Search Report for International Application No. PCT/EP2012/059787 mailed Dec. 5, 2012, 4 pages.
International Search Report for International Application No. PCT/EP2012/059788 mailed Dec. 3, 2012, 4 pages.
International Search Report for International Application No. PCT/EP2013/051163 mailed Mar. 4, 2013, 4 pages.
International Search Report for International Application No. PCT/EP2013/068882 mailed Oct. 30, 2013, 4 pages.
International Search Report for International Application No. PCT/EP2013/068909 mailed Dec. 5, 2013, 4 pages.
International Search Report for International Application No. PCT/EP2014/065840 mailed Oct. 7, 2014, 4 pages.
International Search Report for International Application No. PCT/EP2016/073262 mailed Nov. 18, 2016, 5 pages.
International Search Report for International Application No. PCT/EP2016/073263 mailed Dec. 23, 2016, 3 pages.
International Search Report for International Application No. PCT/EP2017/065163, mailed Aug. 8, 2017, 3 pages.
International Search Report for International Application No. PCT/EP2017/073697 mailed Nov. 6, 2017, 4 pages.
International Search Report for International Application No. PCT/EP2017/074545 mailed Nov. 28, 2017, 3 pages.
International Search Report for International Application No. PCT/EP2017/074079 mailed Dec. 22, 2017, 4 pages.
International Search Report for International Application No. PCT/EP2017/082739 mailed Mar. 6, 2018, 3 pages.
International Search Report for International Application No. PCT/EP2017/083770 (revised version) mailed Jul. 6, 2018, 4 pages.
International Search Report and Written Opinion for International Application No. PCT/EP2017/083770 mailed Jul. 6, 2018, 14 pages.
International Search Report for International Application No. PCT/EP2019/055149 mailed May 27, 2019, 4 pages.
Ishizaki et al., "Treatment of Diabetic Retinopathy", Forum: Complication, Practice, 2009, 26(5): 474-476 (3 pages).
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, N., et al., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., "Management of Dry Eye Disease," The American Journal of Managed Care, 2008, 14 (3), S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4), 1873-1883.
Mantle et al., "Adverse and beneficial effects of plant extracts on skin and skin disorders," Adverse Drug Reaction and Toxicological Reviews, 2001, 20(2): 89-103.
Meinert, H. et al., "Semifluorinated Alkanes—A New Class of Compounds with Outstanding Properties for Use in Ophthalmology," European Journal of Ophthalmology, 2000, 10 (3), 189-197.
Meinert, H. et al., "The Use of Semifluorinated Alkanes in Blood-Substitutes," Biomaterials, Artificial Cells, and Immobilization Biotechnology, 1993, 21 (5), 583-595.
Messmer, E.M., "The Pathophysiology, Diagnosis, and Treatment of Dry Eye Disease," (2015) Deutsches Arzteblatt International, 112(5):71-82.
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Murdan, S., "Enhancing the Nail Permeability of Topically Applied Drugs," Expert Opinion on Drug Delivery, 2008, 5 (11), 1267-1282.
O'Rourke, M. et al., "Enhancing Delivery of Topical Ocular Drops," Cataract & Refractive Surgery Today Europe, 2016, 2 pages.
Perry, H., "Dry Eye Disease: Pathophysiology, Classification, and Diagnosis," The American Journal of Managed Care, 2008, 14 (3), S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, (Abstract only).
Plassmann, M. et al., "Trace Analytical Methods for Semifluorinated n-Alkanes in Snow, Soil, and Air," Analytical Chemistry, 2010, 82 (11), 4551-4557.

(56) References Cited

OTHER PUBLICATIONS

Plassmann, M. et al., "Theoretical and Experimental Simulation of the Fate of Semifluorinated n-Alkanes During Snowmelt," Environmental Science & Technology, 2010, 44(17), 6692-6697.

Rosca-Casian, O. et al., "Antifungal Activity of Aloe vera Leaves," Fitoterapia, 2007, 28, 219-222.

Rosenberg, A., "Effects of Protein Aggregates: An Immunologic Perspective," The AAPS Journal, 2006, 8 (3), E501-E507.

Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.

Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).

Schnetler et al., "Lipid composition of human meibum: a review," S Afr Optom, 2013, 72(2), 86-93.

Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.

SPöler et al., "Towards a New in vitro Model of Dry Eye: The ex vivo Eye Irritation Test," Developments in Ophthalmology, 2010, 45, 93-107.

Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31, No. 8, pp. 498-503.

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).

Stevenson, C., "Characterization of Protein and Peptide Stability and Solubility in Non-Aqueous Solvents," Current Pharmaceutical Biotechnology, 2000, 1, 165-182.

Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.

Tiffany, J.M., "Individual Variations in Human Meibomian Composition," Exp. Eye Res., 1978, 27, 289-300.

Troiano et al., "Effect of Hypotonic .4% Hyaluronic Acid Drops in Dry Eye Patients: A Cross-Study", Cornea 27(10): 1126-1130, 1 page (Abstract Only).

Wang, W., "Lyophilization and Development of Solid Protein Pharmaceuticals," International Journal of Pharmaceutics, 2000, 203, 1-60.

Wong, D. et al., "Perfluorocarbons and Semifluorinated Alkanes," Seminars in Ophthalmology, 2000, 15 (1), 25-35.

Ujiie et al., "Successful Treatment of Nail Lichen Planus with Topical Tacrolimus", Department of Dermatology, 2009.

"What is retinal vitrectomy?" Presented by: Medical Online, Obesity and Diabetes Mellitus, 2005, 4(2): 284-286 (3 pages).

Wirta, David L. et al., "A Clinical Phase II Study to Assess Efficacy, Safety and Tolerability of Waterfree Cyclosporine Formulation for the Treatment of Dry Eye Disease," Ophthalmology 126:792-800 (2019).

Xalatan, Latanoprost Ophthalmic Solution, 50 µg/mL Prostaglandin $F_{2\alpha}$ analogue, Product Monograph, Jul. 21, 2014, 30 pages.

Zakeri et al., "Topical calcipotriol therapy in nail psoriasis", A study of 24 cases, Dermatology Online Journal, 2005.

Zhang et al., "Surface micelles of semifluorinated alkanes in Langmuir-Blodgett monolayers," Phys. Chem. Chem. Phys., 2004, 6:1566-1569.

"EvoTears, Product Description" Accessed Online: Dec. 21, 2023. https://evotears.com/at/das-produkt/ (Year: 2017).

"Novaliq GmbH Begins Phase II Clinical Trial of Cyclasol for the Treatment of Moderate to Severe Dry Eye Disease," (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

Agrahari, et al., "A comprehensive insight on ocular pharmacokinetics," Drug Delivery and Translational Research, vol. 6, No. 6, pp. 735-754, (2016).

Babu, K., et al. "Medical Management of Uveitis—Current Trends," Indian J Opthalmol., vol. 61, No. 6, p. 277-283, (2013).

Cabral et al., "Retinal and choroidal angiogenesis: a review of new targets," International Journal of Retina and Vitreous, vol. 3, No. 31, (2017).

Daull, P., et al. "Distribution of Cyclosporine A in Ocular Tissues After Topical Administration of Cyclosporine A Cationic Emulsions to Pigmented Rabbits," Cornea, vol. 32, No. 3, p. 345-354, (2013); Abstract Only.

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, (2004).

Kerns et al., Drug-Like Properties: Concepts, Structure Design and Methods: from ADME to Toxicity Optimization, Elsevier, Chapter 10, Section 10.4.3, 133, (2008).

Lallemand et al., "Cyclosporine Delivery to the Eye: A comprehensive Review of Academic and Industrial Efforts," European Journal of Pharmaceutics and Biopharmaceutics,, vol. 117, pp. 14-28, (2017).

Rojas-Carabali, W., et al. "Clinical relationships between dry eye disease and uveitis: a scoping review," Journal of Ophthalmic Inflammation and Infection, vol. 13, No. 2, (2023).

Scherer et al., "Eyesol: A Novel Topical Ocular Drug Delivery System for Poorly Soluble Drugs," Drug Development & Delivery, vol. 13, No. 1, pp. 40-44, (2013).

Sheppard et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).

Torkildsen et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans (2017).

Yaoxue Zhuanye Zhishi II (Editor: Jin Xiangqun), Military Medical Science Press, 1st Printing of 2nd Edition, Mar. 2009, p. 158.

Yaoxue Zhuanye Zhishi II (Editor: Jin Xiangqun), Military Medical Science Press, 1st Printing of 2nd Edition, Mar. 2009, p. 158, 3 pages (English Machine Translation).

* cited by examiner

OPHTHALMIC COMPOSITIONS COMPRISING TAFLUPROST FOR THE TREATMENT OF GLAUCOMA

CROSS-REFERENCE TO RELATED APPLICATIONS

This application is a U.S. National Stage application under 35 U.S.C. § 371 of International Application No. PCT/EP2019/060455, filed on Apr. 24, 2019, which claims priority to and the benefit of European Application No. 18169920.8, filed on Apr. 27, 2018, the contents of each of which are hereby incorporated by reference in their entireties.

FIELD OF THE INVENTION

The present invention relates to the field of pharmacotherapy. More specifically, it relates to the treatment of diseases and conditions affecting the eye such as glaucoma, increased intraocular pressure, ocular hypertension and/or a symptom associated therewith.

BACKGROUND OF THE INVENTION

Increased intraocular pressure is a frequent disorder of the eye which is often associated with optic nerve damage, in which case the disease is glaucoma. In the absence of optic nerve damage, the condition is referred to as ocular hypertension. Normal intraocular pressure is usually defined as being in the range from 10 to 21 mmHg. The pressure results predominantly from balance between the production rate and the drainage rate of the aqueous humour in the eye. In addition, it is influenced by the corneal thickness and rigidity. The intraocular pressure typically fluctuates around about 15 to 16 mmHg with amplitudes of up to 6 mmHg. For example, it usually decreases in the night due to a decreased production of aqueous humour. It also responds to various physiological factors such as exercise, heart rate, respiration, fluid intake, as well as certain types of systemic or topical drugs.

The aqueous humour is produced by the ciliary bodies of the eye, from where it flows into the posterior chamber. The composition of the aqueous humour is very similar to that of blood plasma but differs from the latter by a lower protein content. Its main constituents are water (99%), electrolytes (inorganic ions to maintain the physiological pH), low amounts of albumin and β-globulins, ascorbate, glucose, lactate, and amino acids.

From the posterior chamber, the aqueous humour is distributed via the pupil of the iris into the anterior chamber of the eye. From here, it flows through the so-called trabecular meshwork, which is a spongy tissue area lined by trabeculocytes whose main function is to drain the humour into a set of tubes called Schlemm's canal, from where the humour enters the blood circulation. The humour flow from the trabecular meshwork into the Schlemm's canal occurs via two different routes: either directly via the aqueous vein to the episcleral vein, or indirectly via collector channels to the episcleral vein by intrascleral plexus. This trabecular outflow pathway accounts for the major fraction of drained aqueous humour. In addition, there exists a second major drainage pathway which is the uveoscleral outflow, which is relatively independent of the intraocular pressure and normally accounts for only 5 to 10% of the aqueous humour drainage in healthy humans.

Both in the trabecular meshwork and in the uveoscleral tissue, various prostanoid receptors have been found, which indicates that prostanoids are involved in the regulation of aqueous humour production and/or drainage and thereby influence the intraocular pressure. In the trabecular network, genes encoding the EP, FP, IP, DP and TP receptor families are expressed, whereas the EP and FP receptor families are dominant in the uveoscleral tissue (Toris et al., Surv Ophthalmol. 2008; 53, Suppl. 1, S107-S120).

Prostanoids are physiological fatty acid derivatives representing a subclass of eicosanoids. They comprise prostaglandins, prostamides, thromboxanes, and prostacyclins, all of which compounds are mediators involved in numerous physiological processes. Natural prostaglandins such as $PGF_{2\alpha}$, $PGE_2$, $PGD_2$, and $PGI_2$ exhibit a particular affinity to their respective receptors (FP, EP, DP, IP), but also have some non-selective affinity for other prostaglandin receptors (ibid.). Prostaglandins also have direct effects on matrix metalloproteinases. These are neutral proteinases expressed in the trabecular meshwork which play a role in controlling humour outflow resistance by degrading the extracellular matrix.

Several prostaglandin analogues have been found effective as topically administered medicines in reducing the intraocular pressure, such as latanoprost, bimatoprost, tafluprost, travoprost and unoprostone. By some experts, bimatoprost is understood as a prostamide rather than prostaglandin derivative.

Latanoprost, travoprost, tafluprost and probably also bimatoprost are potent and selective $PGF_{2\alpha}$ agonists. Their net effect is a reduction of intraocular pressure, which is predominantly caused by a substantial increase in aqueous humour drainage via the uveoscleral pathway. Probably they also increase the trabecular outflow to some degree.

Various eye drop formulations comprising prostaglandin analogues have been developed and are commercially available. Tafluprost is available in preserved formulations as well as in a non-preserved formulation in single-dose containers. The tafluprost formulations have a strength of 15 µg/mL (0.0015%) and additionally contain the surfactant, polysorbate 80. Bimatoprost is also marketed as a buffered, isotonised, and preserved aqueous solution; its strength is 0.3 mg/mL (0.03%). The strength of the commercial unoprostone formulation is 1.5 mg/mL (0.15%). It contains buffer, a preservative, an isotonising agent, and polysorbate 80.

However, preserved aqueous formulations for ophthalmic use are disadvantageous in that they are capable of producing irritancies or hypersensitivity reaction, in particular in long-term use, such as in glaucoma therapy. The most common preservative in the formulations mentioned above is benzalkonium chloride, a quaternary ammonium compound which is associated with frequent irritant toxic reactions. Non-preserved single use containers avoid this disadvantage, but they are expensive. Not only do they require a container for each single dose, but also an overfill of the formulation, which means that a substantial fraction (if not most) of the actual medicine remains in the container and is discharged as waste. Considering the drug in an eye drop which is actually administered into the eye, only a fraction of that becomes effective due to the limited volume capacity of the lacrimal sac: a significant fraction of the administered fluid volume is expelled by the blinking of the eyelids, and another fraction is taken up systemically via the nasolacrimal duct, which potentially leads to adverse drug effects.

Taflotan® (tafluprost) 0.0015% eye drops solution and associated names has been approved for the reduction of elevated intraocular pressure in adult patients with open angle glaucoma and ocular hypertension. Taflotan is a sterile, isotonic, buffered aqueous solution of tafluprost at a concentration of 15 μg/mL. One drop of the aqueous solution contains approximately 0.45 μg of tafluprost and is intended for topical administration to the eye. The recommended daily dose for adults is one eye drop (corresponding to approximately 0.45 μg of tafluprost) to be administered to the affected eye (s), with an optimal effect obtained if administered in the evening.

EP2547323 describes pharmaceutical compositions for the treatment of increased intraocular pressure based on semifluorinated alkanes. Preferred active ingredients include poorly water-soluble prostaglandin analogues such as, for example latanoprost, bimatoprost, tafluprost, travoprost and unoprostone. The compositions can be administered topically into the eye.

WO2018033854 describes an ophthalmic aqueous solution for treating ocular hypertension and glaucoma comprising tafluprost in an amount of 0.0001 to 0.0010% (w/v), polyacrylic acid and substantially no preservatives. The formulations described in WO2018033854 have a lower concentration of the active ingredient than the currently commercially available product, are preservative free and have a low viscosity.

It is an object of the present invention to provide a novel pharmaceutical composition which is useful in a method of prevention or therapy of glaucoma, increased intraocular pressure, ocular hypertension or a symptom associated therewith, which overcomes at least one of the limitations or disadvantages associated with prior art formulations. In a specific aspect, it is an object of the invention to provide an ophthalmic composition which has the capacity to incorporate substantial amounts of poorly water-soluble drug substances useful in the management of glaucoma, increased intraocular pressure, ocular hypertension or a symptom associated therewith. Further objects of the invention will become clear on the basis of the following description, examples, and patent claims.

SUMMARY OF THE INVENTION

In a first aspect, the invention relates to a pharmaceutical composition for use in the prevention or therapy of glaucoma, increased intraocular pressure, ocular hypertension and/or a symptom associated therewith, wherein the composition comprises tafluprost and a liquid vehicle comprising a semifluorinated alkane.

In a further aspect, the present invention provides a kit comprising a pharmaceutical composition for use according to the first aspect of the invention, wherein the kit comprises a container for holding the pharmaceutical composition and a drop dispenser for administering the composition.

DETAILED DESCRIPTION OF THE INVENTION

Figure 1:
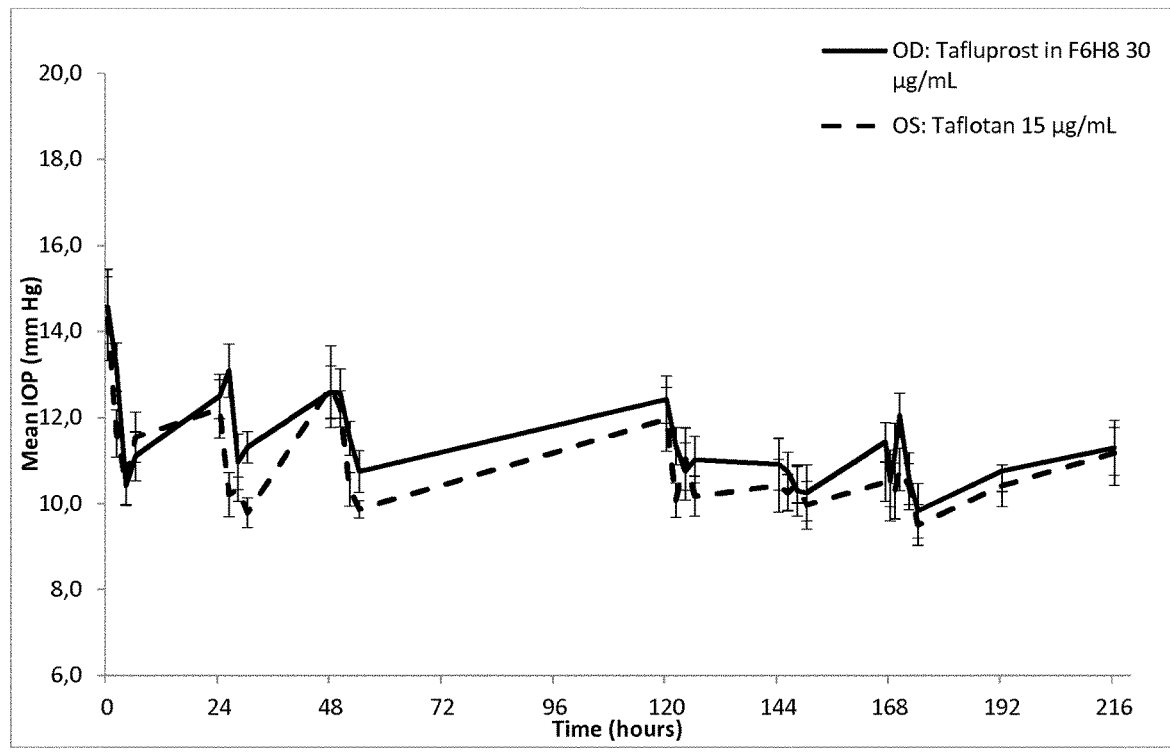
FIG. 1 and FIG. 2 show the results of two tests of the experimental animal study (dog) further outlined below, in which the pharmacodynamics with regard to intraocular pressure (IOP) after repeated topical ocular administration of tafluprost has been investigated in comparison with administration of Taflotan®.

In a first aspect, the present invention relates to a pharmaceutical composition for use in the prevention or therapy of glaucoma, increased intraocular pressure, ocular hypertension and/or a symptom associated therewith, wherein the composition comprises tafluprost and a liquid vehicle comprising a semifluorinated alkane.

The pharmaceutical composition according to the present invention is useful for the treatment or prevention of glaucoma and/or a symptom associated therewith, for example such as the symptoms described below. Glaucoma as understood herein is a term for eye conditions which damage the optic nerve, and which can lead to a loss of vision. The primary division in categorizing different types of glaucoma is open-angle and closed-angle (or angle-closure) glaucoma. The open angle refers to the angle where the iris meets the cornea being as wide and open as it should be, allowing the fluid from inside the eye to drain, thus relieving the internal pressure. Where this angle is narrowed or closed, pressure can build up, and eventually damage the optic nerve leading to loss of vision.

The pharmaceutical composition according to the present invention is also useful for the treatment or prevention of increased intraocular pressure (IOP) and/or a symptom associated therewith, for example such as the symptoms described below. IOP as understood herein constitutes a major risk factor for the development of glaucoma. IOP is the main cause of damage to the optic nerve and is characterized by an excessive fluid pressure within the eye, which can be due to various reasons including blockage of drainage ducts, and narrowing or closure of the angle between the iris and cornea. Elevated IOP represents a major risk factor for glaucomatous field loss. The higher the level of IOP, the greater the likelihood of optic nerve damage and visual field loss.

Furthermore, the pharmaceutical composition according to the present invention is useful for the treatment or prevention of ocular hypertension and/or a symptom associated therewith, for example such as the symptoms described below. The term ocular hypertension as understood herein denotes the presence of elevated fluid pressure inside the eye, usually, however, with no optic nerve damage or visual field loss. Elevated intraocular pressure is an important risk factor for glaucoma. For most individuals, the normal range of intraocular pressure is between 10 mmHg and 21 mmHg. Most individuals with consistently elevated intraocular pressures of greater than 21 mmHg, particularly if they have other risk factors, are therefore usually treated in an effort to prevent vision loss from glaucoma which may result from ongoing ocular hypertension. Ocular hypertension may be considered as a result of an imbalance between the fluid that enters the eye through the ciliary body and the fluid that exits the eye through the trabecular meshwork.

The composition for the use according to the present invention comprises the active ingredient tafluprost with the empirical formula $C_{25}H_{34}F_2O_5$ and molecular weight of 452.5 g/mol (CAS Number 209860-87-7). Tafluprost is a colourless to yellow light viscous liquid. It is a prostaglandin F2-alpha analogue, more specifically a prostanoid selective FP receptor agonist that is believed to reduce the intraocular pressure (IOP) by increasing the outflow of aqueous humour. Studies in animals and man suggest that the main mechanism of action is increased uveoscleral outflow.

In preferred embodiments, the pharmaceutical composition for the use according to the present invention comprises from about 0.0020% to about 0.0050% (w/v) of the active ingredient tafluprost, preferably from about 0.0025% to about 0.0045% (w/v) of the active compound tafluprost, more preferably from about 0.0030% to about 0.0040% (w/v) of the active ingredient tafluprost. In a most preferred embodiment, the pharmaceutical composition for the use according to the present invention comprises from about 0.0025% to about 0.0035% (w/v) of the active ingredient tafluprost. In the present invention, the pharmaceutical composition for the use of the present invention may comprise tafluprost in an amount of about 0.0030% (w/v) with respect to the total volume of the composition.

Unless otherwise indicated, the term "% (w/v)" as used throughout herein in connection with the present pharmaceutical composition denotes the amount of a component of a composition (such as, for example, tafluprost) as a weight percentage in relation to the total volume of the composition (with 'w' denoting the weight and 'v' denoting volume). For example 0.005% (w/v) may be understood as relating to 0.05 mg of a component in 1 mL of the composition, and 0.1% (w/v) would correspond to 1.0 mg of a component in 1 mL of the composition. Unless otherwise indicated, the term "% (w/w)" refers to the amount of a component of a composition as a weight percentage in relation to the total weight of the composition (with 'w' denoting weight). Unless otherwise indicated, the term "% (v/v)" refers to the amount of a component of a composition as a volume percentage in relation to the total volume of the composition (with 'v' denoting volume).

The term 'about' as used herein and in reference or connection to a parameter, for example such as the concentration of tafluprost in the composition or the amount of tafluprost featured in a single dose of the composition, includes the precise value as defined, as well as any value falling within the degree of variability usually observed in measuring or determining these parameters using the standard techniques and equipment known in the art and field.

The pharmaceutical composition according to the present invention further comprises a semifluorinated alkane. The active component tafluprost as described above may be dissolved or suspended, preferably dissolved in the liquid vehicle comprising a semifluorinated alkane as described below. The term "semifluorinated alkane" or "SFA" used synonymously throughout herein denotes a compound consisting of a perfluorinated hydrocarbon segment attached to a non-fluorinated hydrocarbon segment. Both segments may be branched or linear. Preferably, however, both segments are unbranched, linear segments.

In preferred embodiments, the pharmaceutical composition comprises a semifluorinated alkane or a mixture of two or more different semifluorinated alkanes. Preferably, however, the present pharmaceutical composition comprises just one semifluorinated alkane.

In the present invention, preferred semifluorinated alkanes are those of the general formula (I)

$$CF_3(CF_2)_n(CH_2)_mCH_3 \quad (I),$$

wherein the index n is an integer selected from 3 to 7, and m is an integer selected from 4 to 7.

An alternative nomenclature for the specified semifluorinated alkanes as noted in parentheses below and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-perfluorobutyl-pentane or $CF_3(CF_2)_3$—$(CH_2)_4CH_3$ (which may be also, alternatively expressed as formula $F(CF_2)_4(CH_2)_5H$), which has a linear perfluorinated segment F with four carbons (n=4) and a linear non-fluorinated hydrocarbon segment with five carbons (m=5). Furthermore, F6H8 may be used to denote 1-perfluorohexyl-octane or $CF_3(CF_2)_5$—$(CH_2)_7CH_3$ (which may be also, alternatively expressed as formula $F(CF_2)_6(CH_2)_8H$), which has a linear perfluorinated segment F with six carbons (n=6) and a linear non-fluorinated hydrocarbon segment with 8 carbons (m=8).

Accordingly, said semifluorinated alkane as used in the composition of the present invention may be selected for example from $CF_3(CF_2)_3$—$(CH_2)_4CH_3$ (F4H5), $CF_3(CF_2)_3$—$(CH_2)_5CH_3$ (F4H6), $CF_3(CF_2)_3$—$(CH_2)_6CH_3$ (F4H7), $CF_3(CF_2)_3$—$(CH_2)_7CH_3$ (F4H8), $CF_3(CF_2)_4$—$(CH_2)_4CH_3$ (F5H5), $CF_3(CF_2)_4$—$(CH_2)_5CH_3$ (F5H6), $CF_3(CF_2)_4$—$(CH_2)_6CH_3$ (F5H7), $CF_3(CF_2)_4$—$(CH_2)_7CH_3$ (F5H8), $CF_3(CF_2)_5$—$(CH_2)_4CH_3$ (F6H5), $CF_3(CF_2)_5$—$(CH_2)_5CH_3$ (F6H6), $CF_3(CF_2)_5$—$(CH_2)_6CH_3$ (F6H7) and $CF_3(CF_2)_5$—$(CH_2)_7CH_3$ (F6H8). More preferably, said semifluorinated alkane may be selected from $CF_3(CF_2)_3$—$(CH_2)_4CH_3$ (F4H5) and $CF_3(CF_2)_5$—$(CH_2)_7CH_3$ (F6H8).

In a preferred embodiment, the pharmaceutical composition for the use according to the present invention comprises a semifluorinated alkane of formula (I) which is selected from 1-perfluorohexyl-octane ($CF_3(CF_2)_5$—$(CH_2)_7CH_3$ (F6H8)) and 1-perfluorobutyl-pentane ($CF_3(CF_2)_3$—$(CH_2)_4CH_3$ (F4H5)). In a particular preferred embodiment of the present invention, the semifluorinated alkane of formula (I) is 1-perfluorohexyl-octane ($CF_3(CF_2)_5$ $(CH_2)_7CH_3$, (F6H8)).

The liquid SFAs as described above are chemically and physiologically inert, colourless and stable. Their typical densities range from 1.1 to 1.7 g/cm³, and their surface tension may be as low as 19 mN/m. SFAs of the FnHm type are insoluble in water but also somewhat amphiphilic, with increasing lipophilicity correlating with an increasing size of the non-fluorinated segment.

It has been found by the inventors that SFAs are particularly suitable as carriers or vehicles in ophthalmic compositions. This is based on the fact that SFAs are unexpectedly well-tolerated by the eye, as shown in preclinical testing. This is very surprising as organic or non-aqueous solvents, perhaps with the exception of oily compounds, are typically very irritating or even highly damaging when administered to an eye.

The pharmaceutical composition of the invention comprising "a" semifluorinated alkane is to be understood herein, as comprising at least one semifluorinated alkane of Formula (I) as described above. Optionally, however, the composition may comprise more than one, for example, a mixture of two or more semifluorinated alkanes of Formula (I), i.e. of any one of the semifluorinated alkane species as described above.

In yet further embodiment, the pharmaceutical composition may comprise a liquid vehicle consisting of a semifluorinated alkane of Formula (I) as specified above. In this context, the term "a" semifluorinated alkane is to be understood as at least one semifluorinated alkane, but may also include the option of more than one, or a plurality of semifluorinated alkane compounds. Accordingly, in one embodiment, the liquid vehicle may consist of more than one semifluorinated alkane of Formula (I) as specified above.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of'). It is to be understood that isomeric or olefinic impurities that originate from synthesis of semifluorinated alkanes and that are present in only trace or residual amounts as these cannot be quantitatively removed upon purification and that do not confer any technical advantage or relevance in respect of the object of the present invention, do fall under the above definition of such other constituent or component. In contrast, the term 'comprising" or related terms "comprises" or "comprise" in the context of the present compositions, is to be understood as meaning that other features, other than those prefaced by the term may be present in the composition.

In further embodiment, the present pharmaceutical composition as defined in any of the previous embodiments described above, may comprise a semifluorinated alkane or, optionally, a mixture of semifluorinated alkanes in an amount of at least 90 (v/v), 95% (v/v), 98% (v/v), 98.5% (v/v), 99%(v/v), 99.5% (v/v), 99.8% (v/v) or at least 99.9% (v/v), with respect to the total volume of the composition. In a preferred embodiment of the present invention, the pharmaceutical composition for the use of the present invention comprises a semifluorinated alkane in a percentage of from 98.5% to 99.5% (v/v) with respect to the total volume of the composition.

In the present invention, the semifluorinated alkane may be comprised in an amount of from about 98 to 99.8% (w/w), preferably of from 98.5 to 99.5% (w/w), more preferably of from about 99.0 to 99.5% (w/w) with respect to the total weight of the composition. Preferably, the semifluorinated alkane comprised in the pharmaceutical composition for the use of the present invention is present in an amount of up to about 99.4% (w/w) with respect to the total weight of the pharmaceutical composition, more preferably in an amount of about 99.4% (w/w) with respect to the total weight of the pharmaceutical composition.

In further embodiments, the present pharmaceutical composition may further comprise a solubilising agent. The term "solubilizing agent" as used herein denotes a compound or combination of compounds that enhances or facilitates the solubility of the active component tafluprost in the chosen liquid vehicle comprising a semifluorinated alkane as described above. In preferred embodiments, as already mentioned above, tafluprost is completely dissolved in a semifluorinated alkane and optionally a solubilizing agent.

The solubilizing agent, that may be optionally comprised by the present pharmaceutical composition, may preferably be present in an amount of up to 3% (v/v), or preferably of up to 2% (v/v) with respect to the total volume of the pharmaceutical composition. In a preferred embodiment, the solubilising agent is present in amount up to 1.5% (v/v), preferably up to 1.4% (v/v), more preferably up to 1.0% (v/v) with respect to the total volume of the pharmaceutical composition. In another preferred embodiment of the present invention, the solubilising agent is present in an amount of from about 0.5% to 1.5% (v/v), preferably of from about 0.5 to 1.0% (v/v) with respect to the total volume of pharmaceutical composition.

The solubilizing agent, that may be optionally comprised by the present pharmaceutical composition, may preferably be present in an amount of up to 1% (w/w), preferably of up to 0.8% (w/w), more preferably up to 0.6% (w/w) with respect to the total weight of the pharmaceutical composition. In a preferred embodiment, the solubilising agent is present in amount of from 0.2 to 0.7% (w/w), preferably of from 0.4 to 0.6% (w/w) with respect to the total weight of the pharmaceutical composition. In the present invention, a solubilising agent may be comprised in an amount of up to about 0.6% (w/w) with regard to the total weight of the pharmaceutical composition, preferably in an amount of about 0.6% (w/w) with respect to the total weight of the composition.

In some embodiments, the solubilizing agent may be a liquid excipient such as, for example, an organic cosolvent and/or an oil selected from glyceride oils, liquid waxes and liquid paraffin, or an organic solvent exhibiting a high degree of biocompatibility.

Examples of potentially useful liquid excipients comprise oily excipients which may be used in combination with one or more SFA and include triglyceride oils, mineral oil, medium chain triglycerides (MCT), oily fatty acids isopropyl myristate, oily fatty alcohols, esters of sorbitol and fatty acids, oily sucrose esters or any other substance which is physiologically tolerated by the eye. In one of the preferred embodiment, the liquid vehicle comprises a solubilizing agent in form of a liquid excipient.

Further examples of potentially useful solubilizing agents as used herein are organic solvents. Preferred organic solvents include glycerol, propylene glycol, polyethylene glycol and ethanol.

In a preferred embodiment, the pharmaceutical composition may comprise ethanol as the solubilizing agent, preferably in an amount of up to 1.5% (v/v), more preferably in an amount of up to 1.4% (v/v), most preferably in an amount of up to 1.0% (v/v). In a preferred embodiment, the present pharmaceutical composition comprises ethanol in an amount of from 0.5% to 1.5% (v/v), preferably of from 0.5 to 1.0% (v/v) with regard to the volume of the present pharmaceutical composition. In the present invention, the pharmaceutical composition for the use of the present invention may comprise ethanol in an amount of about 1% (v/v) with respect to the total volume of the pharmaceutical composition.

In a preferred embodiment, the pharmaceutical composition may comprise ethanol as the solubilizing agent, preferably in an amount of up to 1% (w/w), more preferably of up to 0.8% (w/w). In a preferred embodiment, the present pharmaceutical composition comprises ethanol in an amount of from 0.5% to 1.5% (w/w), preferably of from 0.5 to 1.0% (w/w), more preferably in an amount of from 0.5 to 0.7% (w/w) with regard to the total weight of the present pharmaceutical composition. In a preferred embodiment, the present pharmaceutical composition comprises ethanol in an amount of about 0.6% (w/w) with respect to the total weight of the pharmaceutical composition.

The pharmaceutical composition for the use according to the present invention may or may not also comprise further excipients, such as, for example, preservatives, more specifically preservatives and/or surfactants. In a preferred embodiment, however, the pharmaceutical composition according to the present invention is substantially free of a preservative.

In a preferred embodiment, the pharmaceutical composition for use according to the present invention is substantially free of water. As understood herein, the term 'substantially free', or alternatively 'essentially free' in reference to a composition constituent refers to the presence of said constituent in no more than trace amounts and that if present in trace amounts the constituent provides no technical contribution to the composition.

In a yet further preferred embodiment, the pharmaceutical composition for the use according to the present invention is substantially free of water and/or of a preservative.

In a particularly preferred embodiment, the pharmaceutical composition for the use according to the present invention comprises tafluprost dissolved in a liquid vehicle comprising 1-perfluorobutyl-pentane ($CF_3(CF_2)_3$—$(CH_2)_4CH_3$ (F4H5)) or 1-perfluorohexyl-octane ($CF_3(CF_2)_5$—$(CH_2)_7CH_3$ (F6H8)) and up to 1% (v/v) of ethanol with respect to the total volume of the liquid vehicle.

In the present invention, the pharmaceutical composition for the use according to the present invention may comprise tafluprost and a) at least 99% (v/v) of 1-perfluorohexyl-octane ($CF_3(CF_2)_5$—$(CH_2)_7CH_3$ (F6H8)) and b) up to 1% (v/v) of ethanol with respect to the total volume of the pharmaceutical composition. Preferably, the pharmaceutical composition for the use according to the present invention consists of tafluprost and a) at least 99% (v/v) of 1-perfluorohexyl-octane ($CF_3(CF_2)_5$—$(CH_2)_7CH_3$ (F6H8)) and b) up to 1% (v/v) of ethanol with respect to the total volume of the pharmaceutical composition.

In a further preferred embodiment, the pharmaceutical composition for the use according to the present invention comprises tafluprost dissolved in a liquid vehicle comprising about 99% (v/v) of 1-perfluorohexyl-octane ($CF_3(CF_2)_5$—$(CH_2)_7CH_3$ (F6H8)) and up to 1% (v/v) of ethanol with respect to the total volume of the liquid vehicle.

In a further preferred embodiment, the pharmaceutical composition for the use according to the present invention comprises tafluprost dissolved in a liquid vehicle essentially consisting of 99% (v/v) of 1-perfluorohexyl-octane ($CF_3(CF_2)_5$—$(CH_2)_7CH_3$ (F6H8)) and 1% (v/v) of ethanol with respect to the total volume of the liquid vehicle.

As outlined above, the composition for the use of the present invention is preferably provided as a clear solution, wherein the tafluprost is fully dissolved in the chosen liquid vehicle. Furthermore, the composition for the use according to the present invention is preferably provided in sterile form.

The pharmaceutical composition for use according to the present invention comprising tafluprost and a semifluorinated alkane may be administered topically to the eye of a subject or may be administered to the eye of a subject by subconjunctival injection. In a preferred embodiment, however, the pharmaceutical composition for use according to the present invention is administered topically to the eye of the subject.

The term "administered topically" as used herein comprises all possible methods of administration which allow the present liquid pharmaceutical composition to be brought in contact with a surface of the eye of a subject. Typically, the present pharmaceutical composition may be administered in the form of a single drop or a plurality of drops or droplets to an eye of a subject. The drop may be administered to the surface of the eye, preferably to any surface region or tissue of the eye that is accessible to topical administration or instillation, for example to the cornea or conjunctiva. The drop or droplet of the composition may be instilled directly onto a surface of the eye, such as the corneal surface of the eye, or alternatively into a space i.e. sac or pocket formed by gently pulling down of the lower eyelid of an eye.

The term "subconjunctival injection" as used herein means any form of injection of the pharmaceutical composition of the present invention below the conjunctiva of the eye of a subject. This may comprise injection of the present pharmaceutical composition by suitable syringes. The term subconjunctivital injection may also comprise injection by a medical device or insert to be inserted below the conjunctiva, e.g. through an generated opening in the conjunctiva.

As used herein, the term 'administration to an eye' or 'per eye' refers to the administration of a given dose, e.g. a single dose, of a pharmaceutical composition for the use according to the invention to an individual eye of a subject. The therapy of the ocular diseases as described herein, namely glaucoma, increased intraocular pressure, ocular hypertension and/or a symptom associated therewith, however, should be understood as being not limited to the treatment of a single eye in a subject, but as being also inclusive of a therapy involving the administration of the composition for the use according to the present invention to each i.e. both eyes of a subject which are affected by said diseases.

The term "subject" as used herein means a human or animal, preferably however a human, suffering from, diagnosed with or endangered by developing glaucoma, increased intraocular pressure, ocular hypertension and/or a symptom associated therewith.

In the present invention, the amount of tafluprost administered in a single dose per eye may be in the range of from about 0.20 µg to 0.55 µg, preferably in the range of from about 0.30 µg to 0.50 µg, more preferably in the range of from 0.30 µg to 0.45 µg. In a preferred embodiment, the amount of tafluprost administered in a single dose per eye may be in the range of from 0.30 to 0.40 µg, preferably of from 0.30 to 0.35 µg, more preferably of 0.33 µg.

The pharmaceutical composition for use according to the present invention forms small droplets (drops). In a preferred embodiment of the present invention, the volume of the composition administered in a single dose per eye, herein referred to as composition "target dose volume per eye", is in the range of about 6 to 28 µl, more preferably in the range of about 6 to 24 µl, and most preferably in the range of about 6 to 15 µl, when administered from a suitable drop dispenser. In another preferred embodiment of the present invention, the pharmaceutical composition for the use according to the present invention has a composition target dose volume per eye in the range of about 8 to 15 µl, preferably in the range of about 9 to 14 µl, most preferably in the range of about 10 to 12 µl. In a most preferred embodiment of the present invention, the composition target dose volume per eye is about 11 µl. This further distinguishes the composition of the present invention from the aqueous tafluprost compositions such as, for example, Taflotan®, that are characterized by droplet sizes of about 30 µl.

Accordingly, in preferred embodiments, the pharmaceutical composition for use in the prevention or therapy of glaucoma, increased intraocular pressure, ocular hypertension and/or a symptom associated therewith, wherein the composition comprises tafluprost and a semifluorinated alkane, the amount of tafluprost administered in a single dose per eye is provided in a defined volume of the pharmaceutical composition (hereinafter referred to as "composition target dose volume per eye"). In further preferred embodiments, the composition target dose volume per eye (containing the amount of tafluprost to be administered in a single dose per eye) is 30 µl or below, preferably lower than 25 µl, more preferably lower than 15 µl, most preferably 11 µl.

In a preferred embodiment of the present invention, the pharmaceutical composition for use according to the present invention comprises from about 0.0025% to 0.0035% (w/v) tafluprost and a liquid vehicle comprising a semifluorinated alkane.

In another preferred embodiment of the present invention, the pharmaceutical composition for use according to the present invention comprises tafluprost and a liquid vehicle comprising a semifluorinated alkane; the composition is administered to the eye of a subject; and the amount of tafluprost administered in a single dose per eye is from 0.30 up to 0.50 µg, preferably from 0.30 up to 0.45 µg, more preferably from 0.30 up to 0.35 µg.

In a particularly preferred embodiment, the pharmaceutical composition for the use according to the present invention comprises about 0.0030% to about 0.0045% (w/v) tafluprost, and the composition is administered in a single dose volume per eye of about 11 µl.

In another preferred embodiment, the pharmaceutical composition for use according to the present invention comprises tafluprost and a liquid vehicle comprising 1-perfluorohexyloctane as a semifluorinated alkane, wherein the composition is administered to the eye of a subject, and wherein tafluprost has a concentration of from about 0.0030 to about 0.0050% (w/v), preferably of from about 0.0030 to about 0.0045% (w/v), more preferably of from about 0.0025 to about 0.0035% (w/v) with respect to the total volume of the composition.

In another preferred embodiment, the pharmaceutical composition for use according to the present invention comprises tafluprost, 1-perfluorohexyloctane and ethanol, wherein the composition is administered to the eye of a subject, wherein the amount of tafluprost administered in a single dose per eye is in the range of from about 0.25 µg to about 0.45 µg, preferably in the range of from about 0.25 µg to about 0.35 µg, more preferably of from about 0.30 µg to about 0.35 µg.

Accordingly, in preferred embodiments, the pharmaceutical composition for use according to the present invention is administered once daily. In further preferred embodiments, the single dose of the pharmaceutical composition for use according to the present invention is administered as one single drop to an eye of a subject.

It has been surprisingly found, that the presence of an SFA as described above allows for the preparation of the present pharmaceutical composition with beneficial combinations of single dose amounts of tafluprost with composition target dose volumes which are advantageous when compared to known aqueous compositions as described above. Specifically, it is possible to achieve a decrease of the intraocular pressure which is comparable to the decrease achieved by administering the commercial composition Taflotan®, which is characterised by a target dose per eye of 0.45 µg and a target dose volume per eye of 30 µl. As shown in FIG. 1, a composition having for example a target dose per eye of 0.33 µg shows a decrease of the intraocular pressure comparable to that of Taflotan®. Further, another advantage of the pharmaceutical composition for the use according to the present invention is that the composition can be administered in considerably lower target dose volumes, compared to the target dose volume of Taflotan®.

As an example, in preferred embodiments, the pharmaceutical composition for use according to the present invention is characterized by the comparable low volume of composition to be administered in a single dose per eye (composition target dose volume), such as about 8 µl to about 15 µl, preferably about 10 µl to about 12 µl, more preferably about 11 µl.

Furthermore, one complication associated with the administration of aqueous compositions with a significantly larger drop size is that usually only fraction of the amount of aqueous composition administered topically to the surface of the eye actually stays there. In many cases, some of the comparatively large volume of the aqueous composition immediately leaks from the surface of the eye and is often wiped off. Therefore, a surplus of composition is often necessary to ensure that the therapeutically effective amount of tafluprost actually reaches the eye.

Based on this, the pharmaceutical composition for the use of the present invention allows for a significant reduction of droplet size and target dose volume associated therewith and therefore, as outlined above for a significant reduction of the total daily dose of tafluprost administered for use in the treatment of glaucoma, increased intraocular pressure, ocular hypertension and/or a symptom associated therewith.

The pharmaceutical composition for the use of the present invention is preferably free of surfactant.

In a second aspect, the present invention provides for a kit comprising a pharmaceutical composition according to the first aspect of the invention, namely for use in the prevention or therapy of glaucoma, increased intraocular pressure, ocular hypertension and/or a symptom associated therewith, wherein the composition comprises tafluprost and a liquid vehicle comprising a semifluorinated alkane, wherein the kit comprises a container for holding the pharmaceutical composition and a drop dispenser for administering the composition.

It is to be understood that all embodiments as described in detail above in connection with the pharmaceutical composition for use according to the first aspect of the invention may be comprised by the kit according to this second aspect of the invention.

As understood herein, the drop dispenser may be a dispenser or applicator means which may be mounted, fixed or connected to the container for holding the pharmaceutical composition. Preferably, the drop dispenser is adapted for dispensing a single dose in the form of a single drop of the pharmaceutical composition according to the first aspect of the invention. More preferably, the drop dispenser is adapted for dispensing a single dose of about 8 µl to about 15 µl volume, preferably of about 10 µl to about 12 µl volume or even more preferably is adapted for dispensing a single dose of about 11 µl volume.

The container for holding the pharmaceutical composition as understood herein is preferably of a volume which may hold a single dose, but more preferably of a volume which may hold multiple or a plurality of doses of the composition.

The container and/or the drop dispenser preferably may be manufactured from a thermoplastic material or polymer. In a one embodiment, the container and/or the drop dispenser is manufactured from a thermoplastic material selected from polyethylene and polypropylene.

In one particular embodiment, the drop dispenser is manufactured from a polyethylene material, preferably selected from low density polyethylene and high density polyethylene, and more preferably is manufactured from a high-density polyethylene. In another embodiment, the container is manufactured from a polypropylene or polyethylene material, and more preferably is manufactured from polypropylene.

Preferably, the container has a volume, or an interior space which is at least partially filled with the pharmaceutical composition for use according to the invention. In a further embodiment, the ratio of the volume of the pharmaceutical composition in the container to the total volume of the container is between 0.4 and 0.7. The total volume of the container, as understood herein refers to the total interior volume formed by the interior dimensions of the container. The volume of the pharmaceutical composition in the container refers to the fill volume, i.e. the volume of the pharmaceutical composition held in the container. For example, in a kit comprising a container with a total volume of 3.0 ml, it is preferred that the container holds a volume of 2.0 ml of a pharmaceutical composition according to the invention. Here, the ratio of the volume of the pharmaceutical composition in the container to the total volume of the container would be about 0.7.

Such kits as provided in accordance with these embodiments may improve storage and dispensability (i.e., ease and consistency in dispensing) of the pharmaceutical composition according to the first aspect of the present invention.

In a third aspect, the present invention refers to a method of treating or preventing glaucoma, increased intraocular pressure, ocular hypertension and/or a symptom associated therewith, the method comprising administering to an eye of a subject, preferably to a human with glaucoma, increased intraocular pressure, ocular hypertension or a symptom associated therewith, a composition comprising tafluprost and a semifluorinated alkane, wherein said method is therapeutically effective in treating glaucoma, increased intraocular pressure, ocular hypertension and/or a symptom associated therewith.

In a fourth aspect, the present invention provides for a pharmaceutical composition for use in a method of prevention or therapy of glaucoma, increased intraocular pressure, ocular hypertension and/or a symptom associated therewith, wherein the composition comprises tafluprost and a semifluorinated alkane, wherein said composition is therapeutically effective in treating or preventing glaucoma, increased intraocular pressure, ocular hypertension and/or a symptom associated therewith.

In a fifth aspect, the present invention relates to a method of reducing the total daily amount of tafluprost administered to a human for the treatment of glaucoma, increased intraocular pressure, ocular hypertension and/or a symptom associated therewith comprising administering once daily to an eye of said human a composition comprising tafluprost and a semifluorinated alkane, preferably comprising tafluprost dissolved at a concentration of 0.0030% (w/v) in a semifluorinated alkane, wherein said method reduces the amount of tafluprost per total daily dose up to 27% and the amount of tafluprost administered in a single dose per eye is at least as therapeutically effective in treating glaucoma, increased intraocular pressure, ocular hypertension and/or a symptom associated therewith as compared to daily administration of a single drop per eye of an aqueous solution comprising 0.0015% (w/v) tafluprost.

In a preferred embodiment of the method according to this fifth aspect of the present invention, the single drop of said composition has a drop volume of about 11 µl and the single drop of said 0.0015% (w/v) tafluprost aqueous solution has a drop volume of about 30 µl.

In a further preferred embodiment of the method according to this fifth aspect of the present invention, the systemic exposure to tafluprost is reduced as compared to daily administration of a single drop of 0.0015% (w/v) tafluprost aqueous solution.

In a yet further preferred embodiment of the method according to this fifth aspect of the present invention, one or more adverse effects are reduced as compared to daily administration of a single drop of 0.0015% (w/v) tafluprost aqueous solution. The term "adverse effects" as used herein means, according to the general meaning, an undesired harmful effect resulting from a medication, in this particular case resulting from topical ocular administration of tafluprost, such as, for example, blurred vision, burning and stinging decreased vision, red eyes, eye pain, headache, cough, swelling of the eye or of the eyelid.

In a sixth aspect, the present invention provides for a method of reducing the total daily amount of tafluprost administered to a human for the treatment of glaucoma, increased intraocular pressure, ocular hypertension and/or a symptom associated therewith, the method comprising administering once daily to an eye of a human with glaucoma, increased intraocular pressure, ocular hypertension and/or a symptom associated therewith a single drop of a composition comprising tafluprost dissolved in F6H8, wherein the amount of tafluprost administered in a single dose per eye is from about 0.30 µg to about 0.35 µg, and wherein said method reduces the amount of tafluprost per total daily dose by up to about 34% and wherein said method is at least as therapeutically effective in treating glaucoma, increased intraocular pressure, ocular hypertension and/or a symptom associated therewith as compared to a once daily administration of a single drop per eye of an aqueous solution comprising 0.0015% (w/v) tafluprost.

It is to be understood that all embodiments as described in detail above in connection with the pharmaceutical composition for use according to the first aspect of the invention may be applied to the methods according to the third to sixth aspect of the present invention.

DETAILED DESCRIPTION OF THE FIGURES

FIG. 1 shows the results of the head to head comparison of a composition comprising tafluprost 0.0030% (w/v) in F6H8 administered to the right eye (OD) of a test animal versus Taflotan® administered to the left eye (OS) of the same test animal as further outlined below. The graph shows the development of the mean introcular pressure (IOP) in mmHg over time.

Figure 2:
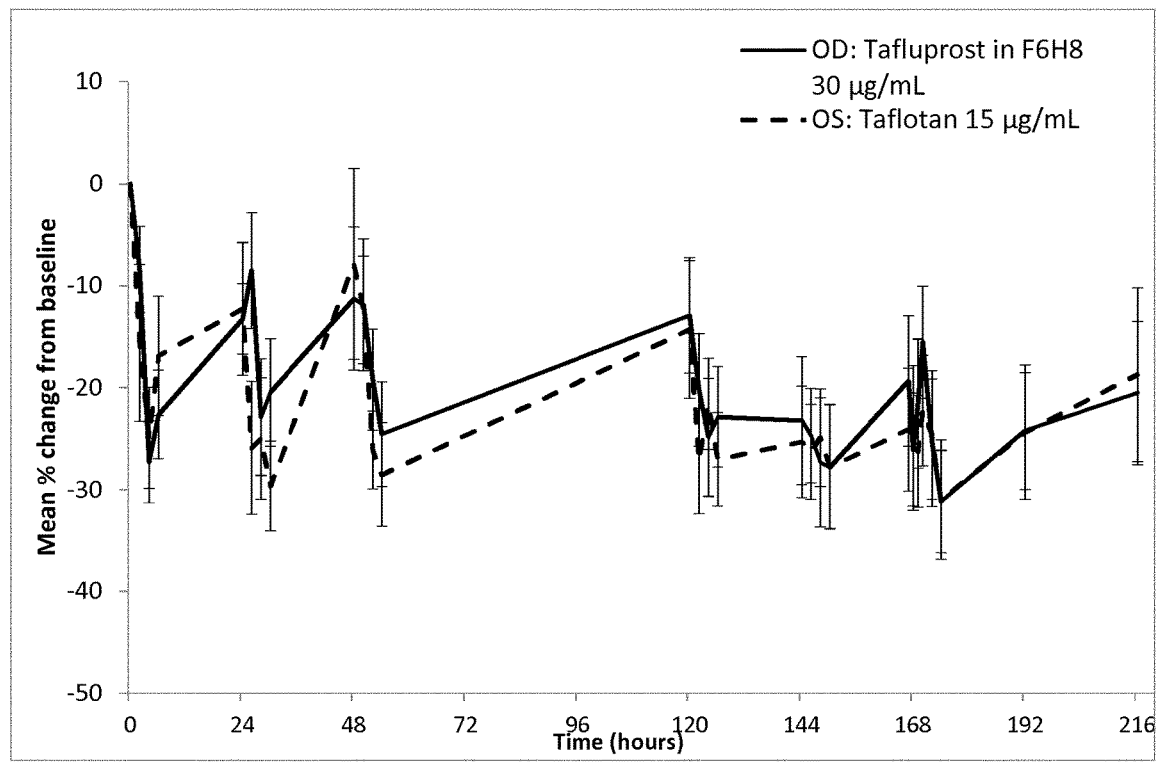

FIG. 2 shows the results of the head to head comparison of a composition comprising tafluprost 0.0030% (w/v) in F6H8 administered to the right eye (OD) of a test animal versus Taflotan® administered to the left eye (OS) of the same test animal as further outlined below. The graph shows the mean % change from baseline of the introcular pressure (IOP) in mmHg over time.

The following list of numbered items are embodiments comprised by the present invention:

1. A pharmaceutical composition comprising tafluprost and a semifluorinated alkane for use in a method of treating glaucoma, increased intraocular pressure, ocular hypertension and/or a symptom associated therewith.
2. The pharmaceutical composition for the use of item 1, wherein the semifluorinated alkane is selected from 1-perfluorohexyloctane or 1-perfluorobutylpentane, preferably 1-perfluorohexyloctane.
3. The pharmaceutical composition for the use of any of the preceding items, wherein the target dose per eye of tafluprost is in the range of from about 0.20 µg to 0.55 µg, preferably in the range of from about 0.30 µg to 0.50 µg, more preferably in the range of from 0.30 µg to 0.45 µg.
4. The pharmaceutical composition for the use of any of the preceding items, wherein the concentration of tafluprost is in the range of from about 0.002 to 0.005% w/v.
5. The pharmaceutical composition for the use of any of the preceding items, wherein tafluprost is dissolved in the semifluorinated alkane.
6. The pharmaceutical composition for the use of any of the preceding items further comprising a solubilizing agent.

7. The pharmaceutical composition for the use of item 6, wherein the solubilizing agent is present at a concentration of from about 0.2 to about 1.5% v/v, preferably from about 0.5 to 1.4% v/v, more preferably from about 0.5 to 1% v/v.
8. The pharmaceutical composition for the use according to any preceding items, wherein the composition is administered to the eye of a subject.
9. The pharmaceutical composition for the use according to item 8, wherein the pharmaceutical composition is administered in a dose volume per eye of 8 to 15 µl, preferably from about 10 to 12 µl.
10. The pharmaceutical composition for the use according to any of the preceding items, wherein the composition is administered once daily to the eye of a subject.
11. The pharmaceutical composition for use according to any one of the preceding items, wherein the composition is administered in a dose volume per eye of 11 µl.
12. The pharmaceutical composition for the use according to any one of the preceding items, wherein the composition is administered to the eye of a subject topically or by subconjunctival injection.
13. The pharmaceutical composition for the use according to any one of the preceding items, wherein the composition is substantially free of water and/or of a preservative and/or of a surfactant, preferably free of water and/or a preservative and a surfactant, more preferably free of water and a preservative and a surfactant.
14. The pharmaceutical composition for the use according to any one of the preceding items, wherein the composition comprises from about 0.0030 to 0.0045% (w/v) tafluprost.
15. The pharmaceutical composition for use according to any one of the preceding items, wherein the composition comprises tafluprost dissolved in a liquid vehicle comprising a) at least 99% (w/w) with respect to the total weight of the composition of 1-perfluorobutyl-pentane $(CF_3(CF_2)_3—(CH_2)_4CH_3$ (F4H5)) and/or 1-perfluorohexyl-octane $(CF_3(CF_2)_5—(CH_2)_7CH_3$ (F6H8)), and b) a solubilising agent, preferably ethanol.
16. The pharmaceutical composition for use according to any one of the preceding items, wherein the composition essentially consists of tafluprost dissolved in a liquid vehicle essentially consisting of a) at least 99% (w/w) with respect to the total weight of the composition of 1-perfluorohexyl-octane $(CF_3(CF_2)_5—(CH_2)_7CH_3$ (F6H8)), and b) a solubilising agent, preferably ethanol.
17. A pharmaceutical composition for use in a method of prevention or therapy of glaucoma, increased intraocular pressure, ocular hypertension or a symptom associated therewith, wherein the composition comprises tafluprost and a semifluorinated alkane.
18. The composition for use according to item 17, wherein the amount of tafluprost administered in a single dose per eye is in the range between about 0.20 to about 0.55 µg, preferably in the range between about 0.25 to 0.35 µg, more preferably in the range between about 0.30 to 0.35 µg.
19. The composition for use according to any of items 17 to 18, wherein the composition target dose volume per eye is from about 8 to about 15 µl, preferably from about 10 to 12 µl.
20. The composition for the use according to any of items 17 to 19, wherein the composition further comprises a solubilising agent, preferably ethanol.
21. The composition for the use according to item 20, wherein the solubilising agent is comprised in an amount of at most 1.5% (v/v) with respect to the total volume of the composition, preferably of at most 1.0% (v/v) with respect to the total volume of the composition.
22. The composition for the use according to any one of items 17 to 21, wherein the semifluorinated alkane is one selected from 1-perfluorohexyl-octane and 1-perfluorobutyl-pentane, preferably 1-perfluorohexyl-octane.
23. The composition for the use according to any one of items 17 to 22, wherein the composition is administered once daily.
24. The composition for the use according to any one of items 17 to 23, wherein the composition is substantially free of water and/or of a preservative and/or of a surfactant, preferably free of water and/or of a preservative and of a surfactant, more preferably free of water and a of preservative and a of surfactant.
25. A kit comprising a pharmaceutical composition for use according to any one of the preceding items, wherein the kit comprises a container for holding the pharmaceutical composition and a drop dispenser for administering the composition.
26. The kit according to item 25, wherein the container for holding the pharmaceutical composition and the drop dispenser are adapted for administering about 8 to 15 µl volume of the composition per drop, preferably 10 to 12 µl volume of the composition per drop, more preferably 11 µl volume of the composition per drop.
27. A method of treating glaucoma, increased intraocular pressure, ocular hypertension or a symptom associated therewith, the method comprising administering to an eye of a subject with glaucoma, increased intraocular pressure, ocular hypertension or a symptom associated therewith, a composition comprising tafluprost and a semifluorinated alkane, wherein the tafluprost is preferably dissolved in the semifluorinated alkane, and wherein said method is therapeutically effective in treating glaucoma, increased intraocular pressure, ocular hypertension or a symptom associated therewith.
28. The method according to item 27, wherein the amount of tafluprost administered in a single dose per eye is from about 0.20 to about 0.55 µg, preferably from about 0.30 to about 0.50 µg, more preferably from about 0.30 to about 0.45 µg.
29. The method according to item 27 or 28, wherein the composition comprises tafluprost at a concentration of from about 0.0020 to 0.0050% (w/v), preferably of from about 0.0030 to 0.0045% (w/v), more preferably of from about 0.0030 to about 0.0040% (w/v).
30. The method according to any one of items 27 to 29, wherein the composition target dose volume per eye is from about 10 to about 12 µl, preferably about 11 µl.
31. The method according to any one of items 27 to 30, wherein the composition further comprises a solubilising agent, preferably ethanol as a solubilising agent.
32. The method according to item 31, wherein the solubilising agent is comprised in an amount of at most 1.5% (v/v) with respect to the total volume of the composition, preferably in an amount of at most 1% (v/v) with respect to the total volume of the composition.

33. The method according to any one of items 27 to 32, wherein the tafluprost administered in a single dose per eye is from about 0.30 to 0.35 µg, preferably 0.33 µg.
34. The method according to any of items 27 to 33, wherein the semifluorinated alkane is one selected from 1-perfluorohexyl-octane and 1-perfluorobutyl-pentane, preferably 1-perfluorohexyl-octane.
35. The method according to any one of items 27 to 34, wherein the composition is administered once daily.
36. The method according to any of the preceding items, wherein the pharmaceutical composition comprises tafluprost dissolved in a solution of about 99% (v/v) of 1-perfluorohexyl-octane and about 1% (v/v) ethanol.
37. The method according to any of the preceding items, wherein the pharmaceutical composition consists of tafluprost dissolved in a solution of at least about 99% (v/v) 1-perfluorohexyl-octane and at most 1% (v/v) ethanol.
38. The method according to any of the preceding items, wherein the composition target dose volume per eye is 11 µl.
39. A method of reducing the total daily amount of tafluprost administered to a human for the treatment of glaucoma, increased intraocular pressure, ocular hypertension or a symptom associated therewith comprising administering once daily to an eye of said human a composition comprising tafluprost and a semifluorinated alkane, wherein the amount of tafluprost administered in a single dose per eye is from about 0.30 to 0.40 µg and wherein said method reduces the amount of tafluprost per total daily dose up to about 34% and is at least as therapeutically effective in treating glaucoma, increased intraocular pressure, ocular hypertension or a symptom associated therewith as compared to daily administration of a single drop per eye of a 0.0015% (w/v) tafluprost aqueous solution.
40. The method of reducing the total daily amount of tafluprost administered to a human for the treatment of glaucoma, increased intraocular pressure, ocular hypertension or a symptom associated therewith according to item 39, wherein the single drop of said composition has a drop volume of about 11 µl and the single drop of said 0.0015% (w/v) tafluprost aqueous solution has a drop volume of about 30 µl.
41. The method of reducing the total daily amount of tafluprost administered to a human for the treatment of glaucoma, increased intraocular pressure, ocular hypertension or a symptom associated therewith according to item 39 or 40, wherein the systemic exposure to tafluprost is reduced as compared to daily administration of a single drop of 0.0015% (w/v) tafluprost aqueous solution.
42. The kit according to any of items 25 or 26, wherein the container and the drop dispenser are adapted for administering a single dose of the pharmaceutical composition or multiple doses.
43. The kit according to item 42, wherein the drop dispenser is adapted to administer a single dose of the pharmaceutical composition.
44. The kit according to any of item 42 or 43, wherein the container is adapted to hold multiple doses of the pharmaceutical composition.

The following examples serve to illustrate the invention, however, should not to be understood as restricting the scope of the invention.

EXAMPLES

Example 1

The study as described below was carried out in order to assess the pharmacodynamics of tafluprost (intraocular pressure, IOP) following repeated topical ocular doses of tafluprost in 1-perfluorohexyloctane (F6H8) in normotensive dogs and to evaluate the pharmacokinetics of tafluprost in aqueous humor. The dog is a suitable species for evaluating ocular distribution and pharmacodynamics of prostaglandin analogs; this model can also provide quantitative pharmacokinetic data.

Study Setup:

The animals were selected for participation in the study based on overall health, body weight, results of ophthalmic examinations, response to IOP challenge, and the following criteria:

healthy, normal ocular surface;
  no invasive ocular procedures for at least one month prior to the study; particularly procedures involving the cornea or ocular anterior segment in general;
  no topical or systemic corticosteroid treatment for at least one month;
  washout from prior topical ocular study medication commensurate with the typical washout period used for clinical studies (at least one week)

Study Design:

The study was performed according to the plan as summarized in Table 1 below. The topical ocular dose (11 or 30 µl, respectively) was administered to the central or superior part of the cornea via a micropipette and allowed to spread across the surface of the eye. After the dose was administered, the eye was allowed to close naturally. Each animal was restrained for approximately one minute to prevent rubbing of the eyes.

TABLE 1

| Phase/ Group | Number of Animals | Topical Ocular Dose Regime OD | Topical Ocular Dose Regime OS | Target Dose Level (µg/eye) OD | Target Dose Level (µg/eye) OS | Target Dose Volume (µL/eye) | Dose frequency |
| --- | --- | --- | --- | --- | --- | --- | --- |
| 1 | 8 | Tafluprost 0.0030% (w/v) in F6H8 | Taflotan 0.0015% (w/v) | 0.33 | 0.45 | 11 (OD); 30 (OS). | QD for 8 d | d Days
IOP Intraocular pressure
OD Right eye
OS Left eye
QD Once daily

Herein described is the preparation of the composition comprising tafluprost 0.0030% (w/v) in F6H8 containing 1% (v/v) ethanol used in the tests of Example 1: 0.030 mg tafluprost (CAS number: 209860-87-7, from Yonsung Fine Chemicals Co.) are dissolved in 0.00791 g ethanol (99.9%) mixed with 1.3221 g F6H8 to yield to a solution having a concentration of 0.0030% (w/v) of tafluprost.

Intraocular pressure was measured for all animals on days 1, 2, 3, 6 and 7 at 0 (immediately predose), 2, 4, and 6 hours postdose and on Day 8 at −1, 0 (immediately predose), 1, 2, 4, 6, 24, and 48 hours postdose. Three readings/eye were taken using a TonoVet.

Study Analysis:

As shown in FIGS. 1 and 2, in the head to head comparison of a composition comprising tafluprost 30 µg/ml in ethanol 1% (v/v) and F6H8 versus Taflotan®, the administration of a solution of tafluprost in F6H8, having a target dose level of 0.33 µg/eye and a target dose volume of 11 µl/eye, shows a decrease of the IOP comparable to that achieved by instilling Taflotan® having a target dose level of 0.45 µg/eye and a target dose volume of 30 µl/eye. The experimental data shows that by using a composition according to the present invention it is possible to achieve a decrease of the IOP comparable to that of the gold standard Taflotan®, even with using a lower target dose of the active ingredient. By using a pharmaceutical composition according to the present invention, it is possible for example to reduce the amount of tafluprost instilled in the eye up to about 27%. Further, the lower target dose can be administered in a volume of for example 11 µl, i.e. in a volume considerably lower than 30 µl, thus allowing a reduction of the amount of composition which is expelled or which it taken up systemically.

The invention claimed is:

1. A method of treating glaucoma, increased intraocular pressure, ocular hypertension and/or a symptom associated therewith, comprising administering to a patient in need thereof, a pharmaceutical composition consisting of 0.002-0.005% (w/v) tafluprost dissolved in a vehicle consisting of a semifluorinated alkane and up to 3% (w/w) of ethanol.

2. The method of claim 1, wherein the semifluorinated alkane is 1-perfluorohexyloctane or 1-perfluorobutyl-pentane.

3. The method of claim 1, wherein the pharmaceutical composition is administered at a target dose per eye of tafluprost in the range of from about 0.20 µg to 0.55 µg.

4. The method of claim 1, wherein the pharmaceutical composition is topically administered as single drop of about 11 µl volume.

5. The method of claim 1, wherein the concentration of tafluprost is 0.003% w/v.

6. The method of claim 1, wherein the concentration of the ethanol is up to 1.5% w/w.

7. The method of claim 1, wherein the composition is administered to the eye of the patient.

8. The method of claim 7, wherein the pharmaceutical composition is topically administered in a dose volume per eye of 8 to 15 µl.

9. The method of claim 1, wherein the composition is administered once daily to the eye of the patient.

10. A pharmaceutical composition consisting of 0.002-0.005% (w/v) tafluprost dissolved in a vehicle consisting of a semifluorinated alkane and up to 3% (w/w) of ethanol.

11. A kit comprising a pharmaceutical composition according to claim 10, wherein the kit comprises a container for holding the pharmaceutical composition and a drop dispenser for topically administering the composition to the eye of a patient.

12. The kit according to claim 11, wherein the drop dispenser is adapted for dispensing a single dose of the pharmaceutical composition.

13. The kit according to claim 11, wherein the container for holding the pharmaceutical composition holds a single dose or a multiple or a plurality of doses of the composition.

14. The pharmaceutical composition of claim 10, wherein the semifluorinated alkane is 1-perfluorohexyloctane or 1-perfluorobutyl-pentane.

15. The pharmaceutical composition of claim 10, wherein the concentration of tafluprost is 0.0030% w/v.

16. The method of claim 2 wherein the semifluorinated alkane is 1-perfluorohexyloctane.

17. The method of claim 6, wherein the concentration of the ethanol is up to 1.0% w/w.

18. The pharmaceutical composition of claim 10, wherein the semifluorinated alkane is 1-perfluorohexyloctane.

19. The method of claim 3, wherein the target dose per eye of tafluprost is 0.33 µg.

* * * * *